United States Patent
Wagner et al.

(10) Patent No.: US 7,872,053 B2
(45) Date of Patent: Jan. 18, 2011

(54) SURFACE ACTIVE ORGANOSILICONE COMPOUNDS

(75) Inventors: Roland Wagner, Bonn (DE); Karl-Heinz Stachulla, Leverkusen (DE); Karl-Heinz Sockel, Leverkusen (DE); Mark Leatherman, Tarrytown, NY (US); George Policello, Seattle, WA (US); Wenqing Peng, Shanghai (CN); Zijun Xia, Shanghai (CN)

(73) Assignee: Momentive Performance Materials GmbH & Co., KG, Leverkusen (DE)

( * ) Notice: Subject to any disclaimer, the term of this patent is extended or adjusted under 35 U.S.C. 154(b) by 967 days.

(21) Appl. No.: 11/690,876

(22) Filed: Mar. 26, 2007

(65) Prior Publication Data

US 2008/0242743 A1    Oct. 2, 2008

(51) Int. Cl.
*C07F 7/00* (2006.01)
*B01F 3/08* (2006.01)

(52) U.S. Cl. ............................... 516/23; 516/9; 516/20; 556/443

(58) Field of Classification Search .................... 516/9, 516/20, 23; 556/443
See application file for complete search history.

(56) References Cited

FOREIGN PATENT DOCUMENTS

| JP | 05230078 A | * | 9/1993 |
|----|------------|---|--------|
| JP | 05271407 A | * | 9/1993 |

OTHER PUBLICATIONS

De Vekki et al. ("Specific Features of Catalytic Hydrosilylation in Siloxane Systems in the Presence of Sulfoxide-Containing Platinum(II) Complexes", Russian Journal of General Chemistry, vol. 71, No. 12, 2001, pp. 191231923. Translated from Zhurnal Obshchei Khimii, vol. 71, No. 12, 2001, pp. 2017-2030).*

Crivello et al. (The synthesis and cationic polymerization of multifunctional silicon-containing epoxy monomers and oligomers, Journal of Polymer Science Part A: Polymer Chemistry, vol. 32 Issue 4, pp. 683-697 (Mar. 1994)).*

* cited by examiner

*Primary Examiner*—Ling-Siu Choi
*Assistant Examiner*—Chun-Cheng Wang
(74) *Attorney, Agent, or Firm*—Rankin, Hill & Clark LLP

(57) ABSTRACT

The present invention relates to new organodisilanes or carbodisilanes, a process for manufacturing the same and their use, in particular, as surface active agents, especially as spreading agents.

19 Claims, No Drawings

SURFACE ACTIVE ORGANOSILICONE COMPOUNDS

FIELD OF THE INVENTION

The present invention relates to new organodisilane or carbosilane compounds a process for manufacturing the same and their use as surface active agents, in particular spreading agents.

The topical application of liquid compositions to the surfaces of both animate and inanimate objects to effect a desired change involve inter alia the processes of controlling wetting, spreading, foaming, detergency, and the like. When used in aqueous solutions to improve the delivery of active ingredients to the surface being treated, new organodisilane or carbosilane compounds have been found to be extremely useful in enabling the control of these processes to achieve the desired effect. Moreover the new organodisilane or carbosilane compounds have been found to be extremely resistant towards extreme environment conditions, in particular they maintain their acitivity in a wide pH range of about 5 to about 10.

BACKGROUND OF THE INVENTION AND PRIOR ART

It is known from the prior art that some specific types of silanes or siloxanes having surface active groups can provide these properties, in particular spreading properties.

For example, alkylenoxide modified tri- and disiloxanes are already disclosed in U.S. Pat. No. 3,299,112 and exhibit very good spreading properties, especially a high spreading velocity. These compounds are proposed for the use as agricultural sprays without undue foaming of the spray mixture as disclosed in U.S. Pat. No. 5,504,054. Such polyether-siloxanes are e.g. available under tradenames like Silwet L 77 (former trade name of Union Carbide) from GE Bayer Silicones. (see for example R. Wagner, Y. Wu, G. Czichocki, H. v. Berlepsch, F. Rexin, L. Perepelittchenko, Silicon-modified surfactants and wetting: II. Temperature-dependent spreading behaviour of oligoethylene glycol derivatives of heptamethyltrisiloxane, Applied Organometallic Chemistry Vol 13, Issue 3 pages 201-208; 611-620, 1999, John Wiley & Sons, Ltd.).

For example Silwet L 77 has the following formula:

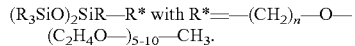

$(R_3SiO)_2SiR—R^*$ with $R^*=—(CH_2)_n—O—(C_2H_4O—)_{5-10}—CH_3$.

EP-A 710500, EP-A 630901 or U.S. Pat. No. 6,489,498 (Goldschmidt) describe mono-functional polyethersiloxanes wherein one endgroup of the polyether is a trialkylsilyl group. DE 41 41 046 (Goldschmidt) describes other trisiloxanes having alkylsulphate groups or salts thereof as side group.

GB 1 520 421 A or EP-A 367381 (Dow Corning) disclose silane or siloxane structures with a hydrophilic group, which does not include polyether groups. The synthesis for these types of silane or siloxane structures utilizes GRIGNARD-reactions based on chloromethyl-trimethylsilane or other silanes.

All of these compounds have one or more disadvantages, i.e. either the spreading properties are not stable under storage at extreme conditions like pH below 5 or above pH 9 and or the spreading effect e.g. the efficiency or the velocity to spread over extended areas is too small. Especially surface active compounds having more than 2 siloxane bonds tends to be unstable at pH values smaller <6 or greater >7.5 are undergoing reactions which lead to non-active compounds in terms of spreading. The manufacturing by GRIGNARD reactions has an significant impact on costs of the precursors.

Compounds having superspreading properties can provide this ability under severe conditions over longer times and they can enhance the action of active substances upon surfaces, wettability of several surfaces like the distribution of plant protection agents on the surfaces of leaves or antifoaming agents or foamstabilizers on the surface of numerous compositions whereby the spreading agent itself can act as defoamer or foam stabilizer.

The expense synthesis going over organometallic coupling reaction like GRIGNARD or WURTZ reactions or expensive precursors like chloromethyl-trimethylsilane imply obviously disadvantages e.g. in costs for a broad application of these compounds.

The surface active compounds in terms of the invention are especially those compounds which have a high resistance against extreme concentrations of proton concentrations, i.e. as well pH values of smaller than 5 and higher than 10. A second feature of these compounds is the ability to spread upon the surface under acidic and basic conditions in a very short time, and maintaining this property over a long time of storage or in the presence of other chemicals.

Furthermore the new compounds can be obtained by a completely new process from cheap intermediates without need for use of organometallic compounds which are expensive and difficult to handle.

Thus the invention provides new structures, new sources of the precursors and new routes of the synthesis for organodisilanes or carbosilanes modified with surface active groups having the ability to maintain its spreading properties over longer time over storage under severe conditions.

Such properties are required in several compositions where active ingredients have to be distributed upon a surface in a short time, especially when used in aqueous solutions to improve the delivery of active ingredients to the surface being treated. The new compounds exhibit properties which are least comparable to the trisiloxane type compounds. However, the trisiloxane compounds may only be used in a narrow pH range, ranging from a slightly acidic pH of 6 to a very mildly basic pH of 7.5. Outside this narrow pH range, the trisiloxane compounds are not stable to hydrolysis undergoing a rapid decomposition. Moreover the new compounds are easy to prepare by a novel process.

SUMMARY OF THE INVENTION

The present invention discloses new compounds of the formula (1):

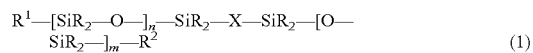

$$R^1—[SiR_2—O—]_n—SiR_2—X—SiR_2—[O—SiR_2—]_m—R^2 \quad (1)$$

wherein:

R is selected from the group of substituents consisting of optionally substituted $C_1$-$C_{22}$ alkyl and optionally substituted $C_6$-$C_{10}$ aryl;

preferably R is methyl;

$R^1$ and $R^2$ are independently from each other selected from organic groups, which are bound via a carbon atom to the silicon atoms, to which they are attached, with the proviso that at least one of $R^1$ and $R^2$ comprises a hydrophilic groups; preferred organic groups are selected from the groups defined under R, especially preferred organic groups are secondary or tertiary $C_3$-$C_{12}$ alkyl or cycloalkyl groups as defined below under non-hydrophilic groups.

X is a single bond or a divalent organic residue, linked over carbon atoms to the silicon atoms, to which the group X is attached, with the exception of —$CH_2$—$CH_2$—;

preferably X is a single bond or methylene (—$CH_2$—), n+m>0, preferably n=0 and m=1.

In the compounds of the invention preferably one of $R^1$ and $R^2$ is a hydrophilic organic group and the other is a non-hydrophilic organic group.

In the compounds of the invention preferably $R^2$ represents a hydrophilic organic group.

In a preferred embodiment of the invention, the compounds of the formula (I) satisfy the following definition:

m=1 and n=0, $R^2$ represents a hydrophilic organic group, $R^1$ represents a non-hydrophilic organic group.

In the compounds of the invention the hydrophilic organic group comprises one or more of the following functional groups:

a polyether group,
a polyetherester group,
an amide group,
an amine N-oxide group,
a sulfate group,
a quaternary ammonium group,
a zwitter ionic group,
a sulfonate group,
a carboxyl group,
a phosphate group,
a hydroxyl group,
sulfosuccinate group.

The most preferred functional group which provides for the hydrophilic properties of the hydrophilic organic group is a polyether group selected from a group of formula (2):

$$\text{—Z—O—}(C_2H_4O)_a(C_3H_6O)_b(C_4H_8O)_cR^3 \tag{2}$$

where

Z is a divalent optionally substituted linear or branched ($C_1$-$C_{10}$) hydrocarbon radical, optionally interrupted by at least one oxo group and/or optionally substituted by a hydroxyl group.

$2 \leq a+b+c \leq 200$ with $a \geq 2$, preferably: $2 \leq a+b+c \leq 20$, $R^3$ is selected from hydrogen, an optionally substituted $C_1$-$C_{22}$ alkyl group, or an optionally substituted $C_1$-$C_{22}$ alkanoyl group, preferably $R^3$ is $C_1$-$C_4$ alkyl.

In the formula (2) the group ($C_2H_4O$) is a group of the formula

—$CH_2$—$CH_2$—O—, the group of the formula ($C_3H_6O$) is a group of the formula

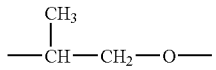

and the group of the formula ($C_4H_8O$) is a group of the formula

—$CH_2$—$CH_2$—$CH_2$—$CH_2$—O—

These alkylene oxide groups can be arranged in any possible order, in particular, block-wise or random-wise.

In formula (2) preferably:

a=2-200, more preferably 2-20; most preferred 2-10;
b=0-20, more preferably 0-5;
c=0-20, more preferably 0-5.

The hydrophilic organic groups for $R^1$ or $R^2$ may also include the following:

—Z—$N^+R_2$—$(CH_2)_p$—$COO^-$(carbobetaine)
—Z—$N^+R_2$—$(CH_2)_p$—$SO_3^-$(sulfobetaine),
—Z—$NO^+R_2An^-$(amine oxide),
—Z—CO—$NR_2$, —Z—$NR_2$—CO—$R^3$ (amide),
—Z—$SO_3^-M^+$(sulfonate),
—Z—O—$SO_3^-M^+$(sulphate),
—Z—O—$PO_3^{2-}2M^+$(phosphate),
—Z—$CO_2^-M^+$(carboxylate),
—Z—$N^+R_3 An^-$(quaternary ammonium groups), wherein R is as defined above, p is 1 to 6, $An^-$ is an anion, e.g. halogenide, carboxylate, sulphate, phosphate, carbonate, etc.

$M^+$ is a cation, e.g. sodium, ammonium, potassium etc.

The preferred reaction pathway to build a Si—Z— bond is the hydrosilylation of alkenyl substituted precursors having other units as defined above, e.g. alkenylethers, alkenylesters, alkyleneepoxides or alkenyl halogenides. The preferred alkenyl group is the allyl group, represented e.g. by allyl substituted polyethers. Further reactions can be necessary for the manufacturing of quaternary ammonium groups, betaines or amine oxides.

The non-hydrophilic group $R^1$ or $R^2$ does not comprise any one of the aforementioned functional groups. Preferably the non-hydrophilic organic group is selected from a $C_1$-$C_{22}$-alkyl group, optionally substituted with one or more fluoro atoms, a $C_6$-$C_{10}$-aryl group, and a $C_6$-$C_{10}$-aryl($C_1$-$C_6$)-alkyl group. The most preferred non-hydrophilic organic group is a $C_1$-$C_{12}$-alkyl group, like for example methyl, ethyl, propyl, n-butyl, n-pentyl, n-hexyl, styryl; especially preferred are iso-propyl, sec.-butyl, tert.-butyl, sec.-pentyl, sec.-hexyl, cyclohexylethyl, limonyl and norbonyl groups.

In a preferred embodiment of the compounds of the invention $R^1$ or $R^2$ represents a hydrophilic organic group selected from polyether groups, which are preferably selected among those of formula (2) above.

The present invention also relates to a novel process for preparing the compounds of the following formula $$R^1\text{—[Si }R_2\text{—O—]}_n\text{—SiR}_2\text{—X—SiR}_2\text{—[O—SiR}_2\text{—]}_m\text{—R}^2 \tag{1'}$$

wherein

R is selected from the group of substituents consisting of optionally substituted $C_1$-$C_{22}$ alkyl and optionally substituted $C_6$-$C_{10}$ aryl, $R^1$ and $R^2$ are independently from each other selected from organic groups, which are bound via a carbon atom to the silicon atoms, to which they are attached, with the proviso that at least one of $R^1$ and $R^2$ comprises a hydrophilic group, X is a single bond or a divalent organic residue, linked over carbon atoms to the silicon atoms, to which the group X is attached, n+m>0, which process comprises the following steps:

a) subjecting a compound of the formula (III)

$$Y\text{—SiR}_2\text{—X—SiR}_2\text{—Y} \tag{III}$$

or a fraction comprising the same, wherein

R and X are as defined above,

Y is independently $R^1$ or a hydrolysable group, with the proviso that at least one of the groups Y is a hydrolysable group, together with an active hydrogen containing compound,
b) optionally separating the reaction product,
c) optionally subjecting the reaction product obtained in step b) to hydrolysis with water,
d) reacting the reaction product obtained in step a), b) or c) with a compound of the formula (IV)

$$H-SiR_2-[O-SiR_2-]_m-H \quad (IV),$$

wherein R and m are each as defined above, to obtain a compound of formula (V):

$$R^4-[SiR_2-O-]_n-SiR_2-X-SiR_2Z-[O-SiR_2-]_m-R^4 \quad (V)$$

$R^4$ is independently $R^1$ or H,
with the proviso that at least one $R^4$ is H,
e) subjecting the Si—H-group(s) to a hydrosilylation reaction with an unsaturated organic compound having a hydrophilic group or a functional group that can be reacted or be transferred respectively to a hydrophilic group $R^1$ or $R^2$,
(step e) is performed according to usual hydrosilylation conditions, that is, the reaction is a radical or metal catalyzed addition reaction of an unsaturated hydrocarbon compound to an SiH-bond. Usually the reaction is carried in temperature range of 0 to 250° C., preferably at 20 to 150° C. at 0.1 to 100 bar with or without additional solvents.)
f) optionally reacting the functional group obtained in step e) with a compound to form the hydrophilic group, and thereby obtaining the compound of formula (I').
In step a) a compound of the formula (III)

$$Y-SiR_2-X-SiR_2-Y \quad (III)$$

or fraction comprising the same, wherein R and X are as defined above, and Y is independently $R^1$ or a hydrolysable group, with the proviso that at least one of the groups Y is a hydrolysable group, is reacted with an active hydrogen containing compound, The hydrolysable group Y is a for example selected from the group which consists of chloro, bromo, $C_1$-$C_{12}$-alkoxy, $C_1$-$C_8$-carbonyloxy, such as acetoxy, amino, aminoalkyl, oximoalkyl and benzamido residues.

The active hydrogen containing compound is preferably selected from compounds having acid hydrogen atoms, like for example water, alcohol, carboxylic acid, ammonia, amines, oximes, enols etc.

In the preferred case where one Y is a hydrolysable group, and the other is for example alkyl, the reaction of
$Y-SiR_2-X-SiR_2-Y$ with water leads to the formation of disiloxane structures of formula:
$Y-SiR_2-X-SiR_2-O-SiR_2-X-SiR_2-Y$, where Y is R or non hydrophilic group $R^1$, for example, is an alkyl group, whereby such disiloxane molecules can have different substituent's Y.

In certain cases it can be appropriate to firstly react the compound $$Y-SiR_2-X-SiR_2-Y$$

with other active hydrogen containing compounds than water like for example alcohol, carboxylic acid, amines, ammonia etc. with the formation of for example compounds of the formula $$Y-SiR_2-X-SiR_2-OR,$$

$$Y-SiR_2-X-SiR_2-NH_2,$$

$$Y-SiR_2-X-SiR_2-NH-R,$$

$$Y-SiR_2-X-SiR_2-OC(O)-R,$$

$$(Y-SiR_2-X-SiR_2-)_2NH,$$

etc.

Those compounds are also finally subjected to the reaction with water (step c)), to form the disiloxane of formula:
$Y-SiR_2-X-SiR_2-O-SiR_2-X-SiR_2-Y$, where Y is for example an alkyl group.

However such an intermediate step of subjecting $Y-SiR_2-X-SiR_2-Y$ with other active hydrogen containing compounds than water might be useful in order to provide purer compounds, by first purifying these intermediates shown above.

The compounds of formula (III) can be synthesized for example by subjecting chlorosilanes to metal-mediated reactions forming Si-Si or Si—X—Si-bonds, or preferably a fraction from the Muller-Rochow-Synthesis is taken, comprising high-boiling methylchlorosilanes, methylchlorodisilanes, methylchlorodisiloxanes and methylchlorocarbosilanes.

Such silanes can be selected from group which consists of pentamethyl-chlorodisilane, 1,1,1,3,3-pentamethyl-3-chlorodisiloxane, 1,1,2,2-tetramethyl-1,2-dichlorodisilane, trimethylsilyl-dimethylchlorosilylmethane, trimethylsilyl-methyldichlorosilylmethane, bis-dimethylchlorosilylmethane 1,1,3,3-tetramethyl-1,3-dichlorodisiloxane, pentamethylmethoxydisilane, trimethylsilyl-dimethyl-methoxysilylmethane and 1,1,1,3,3-pentamethyl-3-methoxydisiloxane.

In step d) the reaction product obtained in step a), b) or c), in particular, the disiloxane of formula:
$Y-SiR_2-X-SiR_2-O-SiR_2-X-SiR_2-Y$, where Y is for example an alkyl group, is reacted with a compound of the formula (IV)

$$H-SiR_2-[O-SiR_2-]_m-H \quad (IV),$$

wherein R and 'm' are each as defined above, to obtain a compound of formula (V):

$$R^4-[SiR_2-O-]_n-SiR_2-X-SiR_2-[O-SiR_2-]_m-R^4 \quad (V)$$

wherein $R^4$ is independently $R^1$ or H,
with the proviso that at least one $R^4$ is H.

The compounds of formula (IV) are well-known to the skilled artisan and are in general commercially available.

Step d) is usually carried out as an acid-catalysed equilibration reaction in a temperature range of for example 10 to 150° C. Typical catalysts include sulfonic acids, such as perfluoroalkyl sulfonic acid, acid catalysts formed 'in-situ' by phosphorus nitriles (e.g. $PNCl_2)_x$, acid activated silicas, clays or char coals, acidic ion exchange resins.

In step d) the compound $$R^4-[SiR_2-O-]_n-SiR_2-X-SiR_2-[O-SiR_2-]_m-R^4 \quad (V)$$

is formed, which may be separated by usual separation techniques, in particular, by distillation.

Thus the present invention also provides novel intermediate compounds of the formula (V):

$$R^4-[SiR_2-O-]_n-SiR_2-X-SiR_2-[O-SiR_2-]_m-R^4 \quad (V),$$

wherein R, X, n, m and $R^4$ are each as defined above, which are, in particular, useful to prepare the compounds of formula (1) by subjecting the intermediates to hydrosilylation as explained above.

The present invention is also related to the use of the novel compounds as a surface active agents, in particular as a wetting agent, a spreading agent, a foam stabilizing agent, a cleansing agent, an impregnating agent, an antistatic agent, a dispersing agent, an emulsifier, a levelling agent, a lubricating agent, an anti-foaming agent, and/or an anti-fogging agent.

Due to their outstanding surface activity, in particular, due to their superspreading activity, the compounds of the invention can find a wide range of possible applications including in an agricultural composition, a laundry composition, a rinse-off composition, a personal care composition, a coating composition, a galvanic composition, a home care composition, cleaning composition, polishing compositions, in detergent compositions, concrete compositions, textile treatment compositions, ink compositions, printing compositions, adhesive compositions, lubricating composition, compositions comprising nano-particles.

Usually and preferably the compounds of the invention are used in compositions together with an active ingredient, which is for example selected from the group of agriculturally active ingredients, a personal care ingredient, including a cosmetically active ingredient, a detergent agent, an anti-corrosion agent, a lubricating agent.

The agriculturally active ingredient is for example selected from the group consisting of pesticides, fungicides, insecticides, herbicides, plant growth regulators and fertilizers.

In a preferred embodiment the compounds of the invention are used in aqueous emulsions wherein the discontinuous phase comprises water and the continuous phase comprises the compounds of the invention, which aqueous emulsions may also comprise the active ingredient as described above.

In another preferred embodiment the compounds of the invention are used in aqueous emulsion wherein the continuous phase comprises water and the discontinuous phase comprises the compounds of the invention, which aqueous emulsions may also comprise the active ingredient as described above.

The compounds of the present invention may also be used in non-aqueous emulsions wherein the discontinuous phase comprises a non-aqueous solvent and the continuous phase comprises the compounds of the invention, optionally together with an active ingredient as explained above.

The compounds of the present invention may also be used in non-aqueous emulsions wherein the continuous phase comprises a non-aqueous hydroxylic solvent and the discontinuous phase comprises the compounds of the invention, optionally together with an active ingredient as explained above.

In the following possible fields of applications of the compounds of the invention or in particular aqueous compositions thereof are shown.

A. As adjuvant in pesticides, agriculture, horticulture, turf, ornamental and forestry:

Many pesticide applications require the addition of an adjuvant to the spray mixture to provide wetting and spreading on foliar surfaces. Often that adjuvant is a surfactant, which can perform a variety of functions, such as increasing spray droplet retention on difficult to wet leaf surfaces, enhance spreading to improve spray coverage, or to provide penetration of the herbicide into the plant cuticle. These adjuvants are provided either as a tank-side additive or used as a component in pesticide formulations.

Typical uses for pesticides include agricultural, horticultural, turf, ornamental, home and garden, veterinary and forestry applications.

The pesticidal compositions of the present invention also include at least one pesticide, where the compounds of the present invention are present at an amount sufficient to deliver between 0.005% and 2% to the final use concentration, either as a concentrate or diluted in a tank mix. Optionally the pesticidal composition may include excipients, co-surfactants, solvents, foam control agents, deposition aids, drift retardants, biologicals, micronutrients, fertilizers and the like. The term pesticide means any compound used to destroy pests, e.g., rodenticides, insecticides, miticides, fungicides, and herbicides. Illustrative examples of pesticides which can be employed include, but are not limited to, growth regulators, photosynthesis inhibitors, pigment inhibitors, mitotic disrupters, lipid biosynthesis inhibitors, cell wall inhibitors, and cell membrane disrupters. The amount of pesticide employed in compositions of the invention varies with the type of pesticide employed. More specific examples of pesticide compounds that can be used with the compounds or compositions of the invention are, but not limited to, herbicides and growth regulators, such as: phenoxy acetic acids, phenoxy propionic acids, phenoxy butyric acids, benzoic acids, triazines and s-triazines, substituted ureas, uracils, bentazon, desmedipham, methazole, phenmedipham, pyridate, amitrole, clomazone, fluridone, norflurazon, dinitroanilines, isopropalin, oryzalin, pendimethalin, prodiamine, trifluralin, glyphosate, sulfonylureas, imidazolinones, clethodim, diclofop-methyl, fenoxaprop-ethyl, fluazifop-p-butyl, haloxyfop-methyl, quizalofop, sethoxydim, dichiobenil, isoxaben, and bipyridylium compounds. Fungicide compositions that can be used with the compounds of the present invention include, but are not limited to, aldimorph, tridemorph, dodemorph, dimethomorph; flusilazol, azaconazole, cyproconazole, epoxiconazole, furconazole, propiconazole, tebuconazole and the like; imazalil, thiophanate, benomyl carbendazim, chlorothialonil, dicloran, trifloxystrobin, fluoxystrobin, dimoxystrobin, azoxystrobin, furcaranil, prochloraz, flusulfamide, famoxadone, captan, maneb, mancozeb, dodicin, dodine, and metalaxyl.

Insecticide, larvacide, miticide and ovacide compounds that can be used with the composition of the present invention, but not limited to, Bacillus Thuringiensis, spinosad, abamectin, doramectin, lepimectin, pyrethrins, carbaryl, primicarb, aldicarb, methomyl, amitraz, boric acid, chlorimeform, novaluron, bistrifluron, triflumuron, diflubenzuron, imidacloprid, diazinon, acephate, endosulfan, kelevan, dimethoate, azinphos-ethyl, azinphos-methyl, izoxathion, chlorpyrifos, clofentezine, lambda-cyhalothrin, permethrin, bifenthrin, cypermethrin and the like.

The pesticide may be a liquid or a solid. If a solid, it is preferable that it is soluble in a solvent, or the compounds of the present invention, prior to application, and the compounds of the invention may act as a solvent, or surfactant for such solubility or additional surfactants may perform this function.

Agricultural Excipients:

Buffers, preservatives, carriers and other standard excipients known in the art also may include the compounds of the invention.

Solvents may also be included in compositions comprising the compounds of the present invention. These solvents are in a liquid state at room temperature (25° C.). Examples include water, alcohols, aromatic solvents, oils (i.e. mineral oil, vegetable oil, silicone oil, and so forth), lower alkyl esters of vegetable oils, fatty acids, ketones, glycols, polyethylene glycols, diols, paraffinics, and so forth. Particular solvents would be 2,2,4-trimethyl, 1,3-pentanediol and alkoxylated (especially ethoxylated) versions thereof as illustrated in U.S. Pat. No. 5,674,832 herein incorporated by reference, or n-methyl-pyrrolidone.

Co-Surfactants:

Moreover, co-surfactants, which have short chain hydrophobes that do not interfere with superspreading as described in U.S. Pat. Nos. 5,558,806; 5,104,647; and 6,221,811 are herein included by reference.

The co-surfactants useful herein include nonionic, cationic, anionic, amphoteric, zwitterionic, polymeric surfactants, or any mixture thereof. Surfactants are typically hydrocarbon based, silicone based or fluorocarbon based.

Useful surfactants include alkoxylates, especially ethoxylates, containing block copolymers including copolymers of ethylene oxide, propylene oxide, butylene oxide, and mixtures thereof; alkylarylalkoxylates, especially ethoxylates or propoxylates and their derivatives including alkyl phenol ethoxylate; arylarylalkoxylates, especially ethoxylates or propoxylates. and their derivatives; amine alkoxylates, especially amine ethoxylates; fatty acid alkoxylates; fatty alcohol alkoxylates; alkyl sulfonates; alkyl benzene and alkyl naphthalene sulfonates; sulfated fatty alcohols, amines or acid amides; acid esters of sodium isethionate; esters of sodium sulfosuccinate; sulfated or sulfonated fatty acid esters; petroleum sulfonates; N-acyl sarcosinates; alkyl polyglycosides; alkyl ethoxylated amines; and so forth.

Specific examples include alkyl acetylenic diols (SURFONYL—from Air Products), pyrrilodone based surfactants (e.g., SURFADONE—LP 100—ISP), 2-ethyl hexyl sulfate, isodecyl alcohol ethoxylates (e.g., RHODASURF DA 530—Rhodia), ethylene diamine alkoxylates (TETRONICS—BASF), and ethylene oxide/propylene oxide copolymers (PLURONICS—BASF) and Gemini type surfactants (Rhodia).

Preferred surfactants include ethylene oxide/propylene oxide copolymers (EO/PO); amine ethoxylates; alkyl polyglycosides; oxo-tridecyl alcohol ethoxylates, and so forth.

B. Coatings, Paints:

Typically coatings formulations may include the compounds of the present invention as a wetting agent or surfactant for the purpose of emulsification, compatibilization of components, leveling, flow enhancement, deairing and the reduction of surface defects. Additionally, the compounds of the invention may provide improvements in the cured or dry film, such as improved abrasion resistance, antiblocking, hydrophilic, and hydrophobic properties. Coatings formulations may exists as, solvent-borne coatings, water-borne coatings and powder coatings.

The coatings components may be employed as: Architecture coatings; OEM-product coatings such as automotive coatings and coil coatings; special purpose coatings such as industrial maintenance coatings and marine coatings; Typical resin types include: Polyesters, alkyds, acrylics, epoxies, polyurethanes.

C. Personal Care

In a preferred embodiment, compositions comprising the compounds of the present invention comprises, per 100 parts by weight ("pbw") of the personal care composition, from 0.1 to 99 pbw, more preferably from 0.5 pbw to 30 pbw and still more preferably from 1 to 15 pbw of the compounds of the invention and from 1 pbw to 99.9 pbw, more preferably from 70 pbw to 99.5 pbw, and still more preferably from 85 pbw to 99 pbw of the personal care composition.

The compositions, comprising the compounds of the present invention may be utilized in personal care emulsions, such as lotions, and creams. As is generally known, emulsions comprise at least two immiscible phases one of which is continuous and the other which is discontinuous. Further emulsions may be liquids with varying viscosities or solids. Additionally the particle size of the emulsions may be render them microemulsions and when sufficiently small microemulsions may be transparent. Further it is also possible to prepare emulsions of emulsions and these are generally known as multiple emulsions. These emulsions may be:

1) aqueous emulsions where the discontinuous phase comprises water and the continuous phase comprises the compounds of the present invention;
2) aqueous emulsions where the continuous phase comprises the compounds of the present invention and the discontinuous phase comprises water;
3) non-aqueous emulsions where the discontinuous phase comprises a non-aqueous hydroxylic solvent and the continuous phase comprises the compounds of the present invention; and
4) non-aqueous emulsions where the continuous phase comprises a non-aqueous hydroxylic organic solvent and the discontinuous phase comprises the compounds of the present invention.

Non-aqueous emulsions comprising a silicone phase are described in U.S. Pat. Nos. 6,060,546 and 6,271,295 the disclosures of which are herewith and hereby specifically incorporated by reference.

As used herein the term "non-aqueous hydroxylic organic compound" means hydroxyl containing organic compounds exemplified by alcohols, glycols, polyhydric alcohols and polymeric glycols and mixtures thereof that are liquid at room temperature, e.g. about 25° C., and about one atmosphere pressure. The non-aqueous organic hydroxylic solvents are selected from the group consisting of hydroxyl containing organic compounds comprising alcohols, glycols, polyhydric alcohols and polymeric glycols and mixtures thereof that are liquid at room temperature, e.g. about 25° C., and about one atmosphere pressure. Preferably the non-aqueous hydroxylic organic solvent is selected from the group consisting of ethylene glycol, ethanol, propyl alcohol, iso-propyl alcohol, propylene glycol, dipropylene glycol, tripropylene glycol, butylene glycol, iso-butylene glycol, methyl propane diol, glycerin, sorbitol, polyethylene glycol, polypropylene glycol mono alkyl ethers, polyoxyalkylene copolymers and mixtures thereof.

Once the desired form is attained whether as a silicone only phase, an anhydrous mixture comprising the silicone phase, a hydrous mixture comprising the silicone phase, a water-in-oil emulsion, an oil-in-water emulsion, or either of the two non-aqueous emulsions or variations thereon, the resulting material is usually a cream or lotion with improved deposition properties and good feel characteristics. It is capable of being blended into formulations for hair care, skin care, antiperspirants, sunscreens, cosmetics, color cosmetics, insect repellants, vitamin and hormone carriers, fragrance carriers and the like.

The personal care applications where the compounds of the present invention and the silicone compositions derived therefrom of the present invention may be employed include, but are not limited to, deodorants, antiperspirants, antiperspirant/deodorants, shaving products, skin lotions, moisturizers, toners, bath products, cleansing products, hair care products such as shampoos, conditioners, mousses, styling gels, hair sprays, hair dyes, hair color products, hair bleaches, waving products, hair straighteners, manicure products such as nail polish, nail polish remover, nails creams and lotions, cuticle softeners, protective creams such as sunscreen, insect repellent and anti-aging products, color cosmetics such as lipsticks, foundations, face powders, eye liners, eye shadows, blushes, makeup, mascaras and other personal care formulations where silicone components have been conventionally added, as well as drug delivery systems for topical application of medicinal compositions that are to be applied to the skin.

In a preferred embodiment, the personal care composition of the present invention further comprises one or more personal care ingredients. Suitable personal care ingredients include, for example, emollients, moisturizers, humectants, pigments, including pearlescent pigments such as, for example, bismuth oxychloride and titanium dioxide coated mica, colorants, fragrances, biocides, preservatives, antioxidants, anti-microbial agents, anti-fungal agents, antiperspirant agents, exfoliants, hormones, enzymes, medicinal compounds, vitamins, salts, electrolytes, alcohols, polyols, absorbing agents for ultraviolet radiation, botanical extracts, surfactants, silicone oils, organic oils, waxes, film formers, thickening agents such as, for example, fumed silica or hydrated silica, particulate fillers, such as for example, talc, kaolin, starch, modified starch, mica, nylon, clays, such as, for example, bentonite and organo-modified clays.

Suitable personal care compositions are made by combining, in a manner known in the art, such as, for example, by mixing, one or more of the above components with the compounds of the invention. Suitable personal care compositions may be in the form of a single phase or in the form of an emulsion, including oil-in-water, water-in-oil and anhydrous emulsions where the silicone phase may be either the discontinuous phase or the continuous phase, as well as multiple emulsions, such as, for example, oil-in water-in-oil emulsions and water-in-oil-in water-emulsions.

In one useful embodiment, an antiperspirant composition comprises the compounds of the present invention and one or more active antiperspirant agents. Suitable antiperspirant agents include, for example, the Category I active antiperspirant ingredients listed in the U.S. Food and Drug Administration's Oct. 10, 1993 Monograph on antiperspirant drug products for over-the-counter human use, such as, for example, aluminum halides, aluminum hydroxyhalides, for example, aluminum chlorohydrate, and complexes or mixtures thereof with zirconyl oxyhalides and zirconyl hydroxyhalides, such as for example, aluminum-zirconium chlorohydrate, aluminum zirconium glycine complexes, such as, for example, aluminum zirconium tetrachlorohydrex gly.

In another useful embodiment, a skin care composition comprises the compounds of the invention, and a vehicle, such as, for example, a silicone oil or an organic oil. The skin care composition may, optionally, further include emollients, such as, for example, triglyceride esters, wax esters, alkyl or alkenyl esters of fatty acids or polyhydric alcohol esters and one or more the known components conventionally used in skin care compositions, such as, for example, pigments, vitamins, such as, for example, Vitamin A, Vitamin C and Vitamin E, sunscreen or sunblock compounds, such as, for example, titanium dioxide, zinc oxide, oxybenzone, octylmethoxy cinnamate, butylmethoxy dibenzoyl methane, p-aminobenzoic acid and octyl dimethyl-p-aminobenzoic acid.

In another useful embodiment, a color cosmetic composition, such as, for example, a lipstick, a makeup or a mascara composition comprises the compounds of the invention, and a coloring agent, such as a pigment, a water soluble dye or a liposoluble dye.

In another useful embodiment, the compounds of the invention and the composition comprising the same are utilized in conjunction with fragrant materials. These fragrant materials may be fragrant compounds, encapsulated fragrant compounds, or fragrance releasing compounds that either the neat compounds or are encapsulated. Particularly compatible with the compounds of the present invention are the fragrance releasing silicon containing compounds as disclosed in U.S. Pat. Nos. 6,046,156; 6,054,547; 6,075,111; 6,077,923; 6,083,901; and 6,153,578; all of which are herein and herewith specifically incorporated by reference.

The uses of the compounds of the present invention are not restricted to personal care compositions, other products such as waxes, polishes and textiles treated with the compositions of the present invention are also contemplated.

D. Home Care

Home care applications include laundry detergent and fabric softener, dishwashing liquids, wood and furniture polish, floor polish, tub and tile cleaners, toilet bowl cleaners, hard surface cleaners, window cleaners, antifog agents, drain cleaners, auto-dish washing detergents and sheeting agents, carpet cleaners, prewash spotters, rust cleaners and scale removers.

The invention will be illustrated by virtue of the following examples.

EXAMPLES

Example 1

Isolation of the Starting Chlorodisilane

Step a) A highboiling methylchlorosilane fraction from the Muller-Rochow-synthesis was subjected to so-called base-catalyzed disilane cleavage reaction. The product obtained was subjected to distillation. The fraction having a boiling point between 100 to 160° C. was separated. The main compounds of the separated fraction have been determined by means of GC/GC-MS. A typical composition is given in Tab. 1

TABLE 1

| Main components of the chlorosilane fraction obtained in step a) | |
|---|---|
| Compound | wt-% |
| $MeSiCl_3$ | 7.0 |
| $Me_3SiSiMe_2Cl$ | 16.7 |
| $Me_2ClSiSiMe_2Cl$ | 23.4 |
| $Me_3SiCH_2SiMe_2Cl$ | 11.1 |
| $Me_3SiCH_2SiMeCl_2$ | 2.8 |
| $MeCl_2SiSiMeCl_2$ | 0.4 | b) A glass column (length 1.2 m, diameter 4 cm, filled with 0.1-0.3 cm long glass pieces) was used to separate the chlorosilane fraction obtained in step a).

Tabs. 2a and 2b summarize the separated fractions and their compositions with respect to the above mentioned higher boiling main compounds (distillation run with 1.7 kg batch).

TABLE 2a

| boiling points and yields | | |
|---|---|---|
| fraction | b.p. range (° C.) | yield (g) |
| low boilers | 40-130 | 318 |
| 1 | 130-135 | 17 |
| 2 | 135-138 | 108 |
| 3 | 138-139 | 85 |
| 4 | 139-141 | 40 |

TABLE 2a-continued boiling points and yields

| fraction | b.p. range (° C.) | yield (g) |
|---|---|---|
| 5 | 141-148 | 206 |
| 6 | 148-150 | 177 |
| 7 | 150-153 | 241 |
| 8 | 153-158 | 82 |

TABLE 2b composition of the fractions

| Fraction | b.p. ° C. | Me$_3$Si—SiMe$_2$Cl | Me$_2$ClSi—SiMe$_2$Cl | Me$_3$SiCH$_2$—SiMe$_2$Cl | Me$_3$SiCH$_2$—SiMeCl$_2$ |
|---|---|---|---|---|---|
| 1 | 130-135 | 45.0 | 4.3 | | |
| 2 | 135-138 | 66.4 | 5.5 | | |
| 3 | 138-139 | 55.1 | 18.0 | | |
| 4 | 139-141 | 45.3 | 20.8 | 3.8 | 0.5 |
| 5 | 141-148 | 22.5 | 35.4 | 9.2 | 0.1 |
| 6 | 148-150 | 2.1 | 63.2 | 12.4 | 2.6 |
| 7 | 150-153 | 0.3 | 60.1 | 23.2 | 6.4 |
| 8 | 153-158 | 0.2 | 35.3 | 38.3 | 12.9 |

The above described steps are repeated in order to get sufficient starting materials for subsequent reactions.

Example 2

Synthesis of Me$_3$SiSiMe$_2$OSiMe$_2$—(CH$_2$)$_3$—(OCH$_2$CH$_2$)$_{6.8}$—OCH$_3$ Step a) Hydrolysis of a Me$_3$SiSiMe$_2$Cl containing cut:

1600 g deionised water are placed in a 4000 ml bottle at ambient temperature. 800 g of a mixture containing the above characterized fractions 1-4 (b.p. range 130-141° C.) are added dropwise under stirring. The mixture is heated to 80-90° C. for 1 hour after the end of the addition. The mixture separates into two phases. The oil phase is dried with sodium sulphate (yield 505 g).

Step b) Synthesis of Me$_3$SiSiMe$_2$OSiMe$_2$H 405.2 g of the hydrolysis product of step a) are mixed with 568.5 g (4.24 mol) MHMH and 1 g C$_4$F$_9$SO$_3$H (perfluorobutansulfonic acid as catalyst). The mixture is heated to reflux for 3 hours. The bulk temperature increases to approx. 100° C. Afterwards, the mixture is cooled to 60° C., mixed with 0.5 g (NH$_4$)$_2$CO$_3$, stirred for 1 hour and filtered.

A first crude distillation yields 142 g of a cut with b.p. 141-150° C. A second distillation of this cut yields 76.8g Me$_3$SiSiMe$_2$OSiMe$_2$H (b.p. 145-150° C., 94.8% GC).

Step c) Synthesis of Me$_3$SiSiMe$_2$OSiMe$_2$—(CH$_2$)$_3$—(OCH$_2$CH$_2$)$_{6.8}$—OCH$_3$: 4.43 g (11.9 mmol) of an allyl polyether of the average formula

CH$_2$=CHCH$_2$—(OCH$_2$CH$_2$)$_{6.8}$—OCH$_3$ and 20 mg of a Pt catalyst [(D$^{vinyl}$)$_4$ modified Pt$^0$ in xylene; 1% Pt content] are mixed at ambient temperature and heated to 60° C. 2.58 g (12.5 mmol) of the Me$_3$SiSiMe$_2$OSiMe$_2$H synthesized under step b) are added dropwise during 20 minutes. The mixture is kept at 60° C. for additional 7 hours.

A volumetric SiH determination shows a 90% conversion of the SiH fluid.

An $^1$H-NMR investigation of the reaction product provides an intensity ratio of

[(CH$_3$)$_3$Si+(CH$_3$)$_2$SiCH$_2$]: (CH$_3$)$_2$SiO= 5:2.17 (theory 5:2)

Further, no signals for the double bond protons CH2=CH— are found anymore.

Example 3

Synthesis of Me$_3$SiCH$_2$SiMe$_2$OSiMe$_2$—(CH$_2$)$_3$—(OCH$_2$CH$_2$)$_{6.8}$—OCH$_3$:

Step a)

Hydrolysis of a Me$_3$SiCH$_2$SiMe$_2$Cl containing cut 750 g deionised water are placed in a 2000 ml bottle at ambient temperature. 500 g of the above characterized fraction 8 (b.p. range 153-158° C.) are added dropwise under stirring. The mixture is heated to 100° C. for 1 hour after the end of the addition. 100 g NaHCO3, dissolved in 1000 g deionized water, are added. After the addition the temperature is maintained at 100° C. for 1 hour. The mixture separates into two phases. The oil phase is dried with sodium sulphate and filtered (yield 271 g).

Step b) Synthesis of Me$_3$SiCH$_2$SiMe$_2$OSiMe$_2$H:

265 g of the hydrolysis product 3a are mixed with 250 g (1.86 mol) MHMH and 0.5 g C$_4$F$_9$SO$_3$H. The mixture is heated to reflux for 4 hours. The bulk temperature increases to approx. 100° C. Afterwards, the mixture is cooled to 70° C., mixed with 2 g (NH$_4$)$_2$CO$_3$, stirred for 1 hour and filtered (yield 473 g).

A first crude distillation yields 210.5 g of a cut with b.p. 155-177° C.

A distillation of this cut yields 46.6 g of a mixture which contains 75% Me$_3$SiCH$_2$SiMe$_2$OSiMe$_2$H and 19% HSiMe$_2$OSiMe$_2$SiMe$_2$OSiMe$_2$H (GC/GC-MS result; b.p. 166-170° C.).

Step c) Synthesis of Me$_3$SiCH$_2$SiMe$_2$OSiMe$_2$—(CH$_2$)$_3$—(OCH$_2$CH$_2$)$_{6.8}$—OCH$_3$:

12.8 g (34.4 mmol) of an allyl polyether of the average formula

CH$_2$=CHCH$_2$—(OCH$_2$CH$_2$)$_{6.8}$—OCH$_3$ are heated to 60° C.

20 mg of a Pt catalyst [(D$^{vinyl}$)$_4$ modified Pt$^0$ in xylene; 1% Pt content] are added. 5 g (26.5 mmol) of the 75% Me$_3$SiCH$_2$SiMe$_2$OSiMe$_2$H containing material synthesized under step b) are added dropwise during 10 minutes. The mixture is kept at 60° C. for additional 3 hours.

A volumetric SiH determination shows a 95.8% conversion of the SiH fluid. An $^1$H-NMR investigation of the reaction product provides an intensity ratio of SiCH$_3$:SiCH$_2$=18.71:2 (theory for a 75% +19% starting material 3b.=19.18:2)

Further, no signal for SiH is found anymore.

Example 4

Property Test

The materials obtained in Examples 2 and 3 were tested on their spreading properties.

The spreading experiments were carried out on smooth polystyrene surfaces (Petri dishes).

32 mg of the aqueous solutions containing the materials from Examples 2 and 3 in the concentrations given in the following tables 3 and tables 4 were placed on the polystyrene surface and the maximum diameter of the drops measured after the end of the spreading process was determined. The low pH or high pH aqueous solutions contained 2% of acetic acid or ethanolamine respectively. The air humidity was in the range from 20 to 45%. The aqueous solutions were stored at room temperature (20 to 23° C.) in glass vials.

TABLE 3a

Spreading behaviour at concentrations of 1, 0.33 and 0.2 wt.-% of compound 3c in water at pH 7

| 3c Time/diameter | 1% [mm] | 0.33% [mm] | 0.2% [mm] |
|---|---|---|---|
| fresh | 11 | 63 | 66 |
| 3 d | 39 | 84 | 84 |
| 45 d | 30 | 65 | 80 |

TABLE 3b

Spreading behaviour at different concentrations of 1, 0.33 and 0.2 wt.-% of compound 3c in water + 2% acetic acid at pH 4.6

| 3c Time/diameter | 1% [mm] | 0.33% [mm] | 0.2% [mm] |
|---|---|---|---|
| fresh | 11 | 56 | 22 |
| 3 d | 40 | 55 | 11 |
| 45 d | 20 | 10 | 10 |

TABLE 3c

Spreading behaviour at different concentrations of 1, 0.33 and 0.2 wt.-% of compound 3c in water + 2% ethanolamine at pH 10

| 3c Time/diameter | 1% [mm] | 0.33% [mm] | 0.2% [mm] |
|---|---|---|---|
| fresh | 22 | 80 | 55 |
| 3 d | 50 | 91 | 91 |
| 45 d | 45 | 45 | 50 |

TABLE 3d

Spreading behaviour at different concentrations of 1, 0.33 and 0.2 wt.-% of compound 2c in water at pH 7

| 2c Time/diameter | 1% [mm] | 0.33% [mm] | 0.2% [mm] |
|---|---|---|---|
| fresh | 43 | 45 | 44 |
| 3 d | 41 | 59 | 42 |
| 45 d | 65 | 57 | 69 |

TABLE 4a

Comparison example: Spreading behaviour at different concentrations of 1, 0.33 and 0.2 wt.-% of compound of Silwet 77 in water at pH 4

| Silwet 77 Time/diameter | 1% [mm] | 0.33% [mm] | 0.2% [mm] |
|---|---|---|---|
| 1 h | <10 | <10 | <10 |

TABLE 4b

Comparison example: Spreading behaviour of different concentrations of of Silwet 77 in water + 2% ethanolamine at pH 10

| Silwet 77 Time/diameter | 1% [mm] | 0.33% [mm] | 0.2% [mm] |
|---|---|---|---|
| 1 h | <10 | <10 | <10 |

The data prove that the materials 2c and 3c are superspreaders. The surface activity can even be maintained over more than 1 h at pH values of 4.6 if appropriate concentrations are chosen. The spreaders 2c or 3c can be synthesized from cheap raw materials using standard operations like distillation, equilibration and hydrosilylation. Expensive metal organic reactions (i.e. Grignard type, metal hydride based reductions etc.) can be avoided.

Further the compounds of the invention show an excellent performance under acidic or as well as extreme basic conditions.

The invention claimed is:
1. A compound of the formula (I):

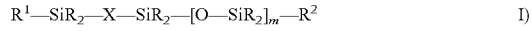

$$R^1\text{—}SiR_2\text{—}X\text{—}SiR_2\text{—}[O\text{—}SiR_2]_m\text{—}R^2 \qquad \text{I)}$$

wherein R is selected from the group consisting of C$_1$-C$_{22}$ alkyl, substituted C$_1$-C$_{22}$ alkyl; C$_6$-C$_{10}$ aryl, and substituted C$_6$-C$_{10}$ aryl, wherein R$^1$ and R$^2$ are independently selected from the group consisting of organic groups bound via a carbon atom to the silicon atoms, provided that at least one of R$^1$ and R$^2$ comprises a hydrophilic group, wherein X is a single bond or a divalent organic residue other than —CH$_2$-CH$_2$—, bound via a carbon atom to the silicon atoms, wherein m>0, and wherein one of R$^1$ and R$^2$ is a hydrophilic organic group and one of R$^1$ and R$^2$ is a non-hydrophilic organic group.

2. The compound of claim 1, wherein m=1.

3. The compound of claim 1, wherein R$^2$ represents a hydrophilic organic group.

4. The compound of claim 1, wherein m=1, R$^2$ represents a hydrophilic organic group, and R$^1$ represents a non-hydrophilic organic group.

5. The compound of claim 1, wherein the hydrophilic organic group is selected from the group consisting of polyethers, polyetheresters, amides, amine-N-oxides, sulfates, quaternary ammonium groups, zwitterionic groups, sulfonates, carboxyl groups, phosphate groups, hydroxyl groups, sulfosuccinate groups, and combinations thereof, wherein the non-hydrophilic group does not comprise any of the foregoing.

6. The compound of claim 1, wherein the non-hydrophilic organic group is selected from the group consisting of $C_1$-$C_{22}$ alkyl, $C_1$-$C_{22}$ alkyl substituted with at least one fluoro atom, a $C_6$-$C_{10}$ aryl, and a $C_6$-$C_{10}$ aryl($C_1$-$C_6$) alkyl group.

7. The compound of claim 1, wherein $R^1$ or $R^2$ represents a polyether group.

8. The compound of claim 7, wherein the polyether group has the formula (2):

$$-Z-O-(C_2H_4O)_a(C_3H_6O)_b(C_4H_8O)_cR^3, \qquad (2)$$

wherein
Z is divalent and selected from the group consisting of linear $C_1$-$C_{10}$ hydrocarbon radicals, branched $C_1$-$C_{10}$ hydrocarbon radicals, substituted linear $C_1$-$C_{10}$ hydrocarbon radicals and substituted branched $C_1$-$C_{10}$ hydrocarbon radicals, wherein
$2 \leq a+b+c \leq 200$, provided that $a \geq 2$, and wherein
$R^3$ is selected from the group consisting of hydrogen, $C_1$-$C_{22}$ alkyl, or substituted $C_1$-$C_{22}$ alkyl.

9. A process for preparing compounds of formula (1')

$$R^1-SiR_2-X-SiR_2-[O-SiR_2]_m-R^2 \qquad (1')$$

wherein R is selected from the group consisting of $C_1$-$C_{22}$ alkyl, substituted $C_1$-$C_{22}$ alkyl; $C_6$-$C_{10}$ aryl, and substituted $C_6$-$C_{10}$ aryl, wherein
$R^1$ and $R^2$ are independently selected from the group consisting of organic groups bound via a carbon atom to the silicon atoms, provided that at least one of $R^1$ and $R^2$ comprises a hydrophilic group, wherein X is a single bond or a divalent organic residue, bound via a carbon atom to the silicon atoms, and wherein m>0,
which process comprises
(a) contacting a compound of formula (III)

$$Y-SiR_2-X-SiR_2-Y \qquad (III)$$

or a fraction comprising the same, wherein
R and X are defined as hereinabove, and Y is independently $R^1$ or a hydrolysable group provided that at least one Y-group is a hydrolyzable group,
together with an active hydrogen-containing compound to form a reaction product;
(b) optionally separating the reaction product;
(c) optionally hydrolyzing the reaction product with water;
(d) reacting the reaction product of (a), (b) or (c) with a compound of the formula (IV)

$$H-SiR_2-[O-SiR_2]_m-H \qquad (IV)$$

wherein R and m are each defined as above to obtain a compound of formula (V)

$$R^1-SiR_2-X-SiR_2-[O-SiR_2]_m-H \qquad (V)$$

(e) subjecting the Si—H group to a hydrosilylation reaction with an unsaturated organic compound having a hydrophilic group or a functional group that can be reacted with a hydrophilic group; and
(f) optionally reacting the functional group obtained in (e) with a compound to form the hydrophilic group to obtain the compound of formula (1').

10. The compound of formula (V), $$R^1-SiR_2-X-SiR_2-[O-SiR_2]_m-H \qquad (V)$$

wherein $R^1$, $R^2$, X, and m are each as defined as in claim 1.

11. A surface active agent comprising the compound of claim 1.

12. A substance selected from the group consisting of a wetting agent, a spreading agent, a foam stabilizing agent, a cleansing agent, an impregnating agent, an antistatic agent, a dispersing agent, an emulsifier, a leveling agent, a lubricating agent, and antifoaming agent and an antifogging agent, wherein the substance comprises the compound of claim 1.

13. A substance selected from the group consisting of an agricultural composition, a laundry composition, a rinse-off composition, a personal care composition, a coating composition, a galvanic composition, a home care composition, a cleaning composition, a polishing composition, a detergent composition, a concrete composition, a textile treatment composition, an ink composition, a printing composition, an adhesive composition, a lubricating composition, and a composition comprising nano-particles, wherein the substance comprises the compound of claim 1.

14. A composition comprising the compound of claim 1 and an active ingredient selected from the group consisting of agriculturally active ingredients, personal care ingredients, cosmetically active ingredients, detergent agents, anticorrosion agents, and lubricating agents.

15. The composition of claim 14, wherein the agriculturally active ingredient is selected from the group consisting of pesticides, fungicides, insecticides, herbicides, plant growth regulators and fertilizers.

16. An aqueous emulsion wherein the discontinuous phase comprises water and the continuous phase comprises the compound of claim 1.

17. An aqueous emulsion wherein the continuous phase comprises water and the discontinuous phase comprises the compound of claim 1.

18. A non-aqueous emulsion wherein the discontinuous phase comprises a non-aqueous solvent and the continuous phase comprises the compound of claim 1.

19. A non-aqueous emulsion wherein the continuous phase comprises a non-aqueous hydroxylic solvent and the discontinuous phase comprises the compound of claim 1.

* * * * *